United States Patent
Imada et al.

(10) Patent No.: US 8,017,111 B2
(45) Date of Patent: Sep. 13, 2011

(54) METHOD OF INTRODUCING SYMBIOTIC FUNGUS INTO PLANT

(75) Inventors: Takahiro Imada, Fujinomiya (JP); Naoya Hiruma, Fujinomiya (JP); Yousuke Kurihara, Fujinomiya (JP); Satoshi Shinozaki, Tokyo (JP); Miho Shimaike, Tokyo (JP); Junya Mizutani, Sapporo (JP)

(73) Assignee: Mayekawa Manufacturing Co., Ltd., Tokyo (JP)

( * ) Notice: Subject to any disclaimer, the term of this patent is extended or adjusted under 35 U.S.C. 154(b) by 731 days.

(21) Appl. No.: 12/073,482

(22) Filed: Mar. 6, 2008

(65) Prior Publication Data

US 2008/0207451 A1  Aug. 28, 2008

Related U.S. Application Data

(62) Division of application No. 10/671,731, filed on Sep. 29, 2003, now abandoned, which is a division of application No. 09/824,590, filed on Apr. 3, 2001, now Pat. No. 6,805,859.

(30) Foreign Application Priority Data

Apr. 5, 2000 (JP) ................................. 2000-103599

(51) Int. Cl.
*A01N 63/00* (2006.01)

(52) U.S. Cl. ...................... 424/93.5; 504/117; 435/254.1
(58) Field of Classification Search ........................ None
See application file for complete search history.

(56) References Cited

OTHER PUBLICATIONS

Porter, et al., J. Agric. Food Chem. (1979), 27(3), 595-8.*
Cagas, et al., Grass and Forage Science (1999), 54(4), 365-37.*
Bush et al., Plant Physiol. (1997) 114: 1-7.*
Murray et al. (1992) Surrogate transformation of perennial ryegrass, *Lolium perenne*, using genetically modified *Acremonium endophyte*. Mol Gen Genet 233: 1-9.*

* cited by examiner

*Primary Examiner* — Irene Marx
(74) *Attorney, Agent, or Firm* — Manabu Kanesaka (57) ABSTRACT

A method of introducing a symbiotic fungus producing one chanoclavine as a final metabolic product into a plant, includes the steps of isolating symbiotic fungi from naturally existing plants, artificially cultivating the isolated symbiotic fungi, introducing the cultivated symbiotic fungi into target plants, infecting the target plants with the introduced symbiotic fungi, determining whether the introduced symbiotic fungi infecting the target plants produce the chanoclavine as the final metabolic product, and selecting the target plants which produce the chanoclavine as the final metabolic product.

10 Claims, 10 Drawing Sheets

Lanes 1, 7, 14: Chanoclavine Sample
Lanes 2, 3, 4, 5, 6, 8, 9, 10, 11, 12, 13: Extracts of plants infected with the endophytes deposited at the Japanese national Institute of Bioscience and Human Technology

Lanes 1,10,17: Chanoclavine sample
Lanes 2,15: Extracts of plants infected with endophytes not deposited at the Japanese National Institute of Bioscience and Human Technology
Lanes 3,16: Extracts of plants infected with endophytes not deposited at the Japanese National Institute of Bioscience and Human Technology + superimposed samples
Lanes 4,6,8,11,13: Extracts of plants infected with the endophytes deposited at the Japanese National Institute of Bioscience and Human Technology
Lanes 5,7,9,12,14: Extracts of plants infected with endophytes not deposited at the Japanese National Institute of Bioscience and Human Technology + superimposed samples

+: Plants infected with the endophytes deposited at the Japanese National Institute of Bioscience and Human Technology
−: Plants infected with endophytes other than those deposited at the Japanese National Institute of Bioscience and Human Technology

FIG. 11

+: Plants infected with the endophytes deposited at the Japanese National Institute of Bioscience and Human Technology
−: Plants infected with endophytes other than those deposited at the Japanese National Institute of Bioscience and Human Technology

FIG. 12

METHOD OF INTRODUCING SYMBIOTIC FUNGUS INTO PLANT

CROSS REFERENCE TO RELATED APPLICATION

This is a divisional application of patent application Ser. No. 10/671,731 filed on Sep. 29, 2003 which is a divisional application of patent application Ser. No. 09/824,590 filed on Apr. 3, 2001, now U.S. Pat. No. 6,805,859.

BACKGROUND OF THE INVENTION AND RELATED ART STATEMENT

The present invention relates to a method of introducing a symbiotic fungus into a plant. More particularly, the present invention relates to a method of introducing an endophyte whose final metabolic product is a chanoclavine to a plant.

Japanese Patent Publication (Kokai) No. 05-317092 has disclosed a method of artificially introducing an endophyte to perennial rye grass. In the method, a test is first performed to confirm whether the endophyte is living in a plant tissue such as callus derived from perennial rye grass. After the callus is confirmed to contain no endophyte, the endophyte is introduced into the callus and the plant tissue is reproduced.

A symbiotic fungus, i.e. the endophyte, is a filamentous fungus living in a plant tissue. It is know that a plant infected by such a filamentous fungus has improved resistance to pests and diseases, better growth rate, and resistance to environmental stresses such as heat and dryness, as compared with a plant with no infection. Thus, it is possible to improve plant characteristics through artificial infection of the endophyte.

Figure 1:
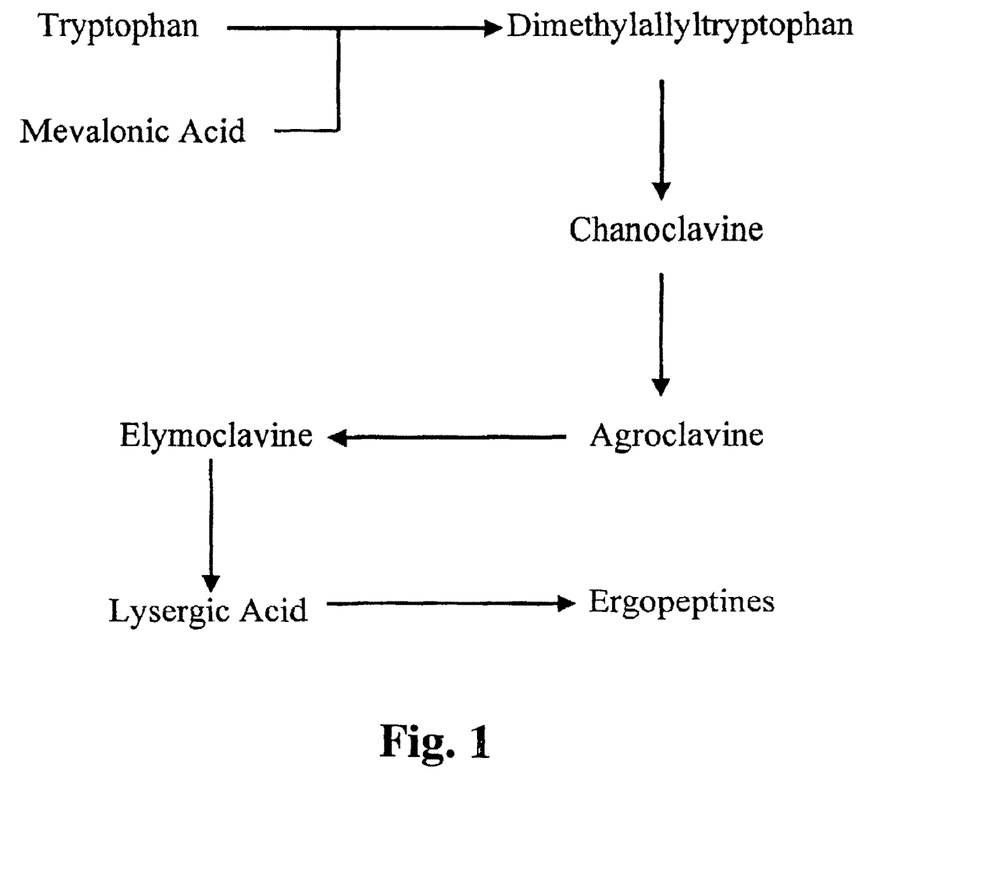
FIG. 1 is a flowchart showing alkaloid metabolism of a symbiotic fungus.

A symbiotic fungus capable of infecting and living in a plant successively biosynthesizes metabolic products as shown in FIG. 1. An end product of the biosynthesis is an ergopeptine such as ergovaline or ergotamine.

It is known that a grass symbiotically infected by the endophyte shows toxicity due to the presence of ergoto alkaloids. The toxicity is considered to be a problem in husbandry as it affects livestock. In the case of pasture, for example, grasses infected with the endophyte such as perennial rye grass and tall fescue are very commonly distributed, and cases of poisoning have been reported due to the ergoto alkaloids.

Rye grass slugger was first reported in New Zealand in 1906, and has occurred mainly in two countries in Oceania, i.e. New Zealand and Australia. The rye grass slugger occurs when the endophyte infects perennial rye grass withered in a severe dry condition from summer to autumn, and livestock such as sheep eat the grass.

In the rye grass slugger, when livestock eat the grass, the livestock show various symptoms, i.e. stiffen limbs and shaking neck, shoulder and flank. In other words, a kind of spasm occurs, and if the symptom continues, the animals become weaker. In the worst case, they are no longer able to move and may starve to death. It has now become clear that the substance responsible for the rye grass slugger is Lolitrum B, a Lolitrum alkaloid.

Fescue toxicosis mainly occurred in the southeast of the U.S. Cows consumed tall fescue, and suffered serious weight loss, and did not eat sufficient fodder. Their milk production declined, and their birth rate also fell. The cows had eaten grasses infected by endophytes, and ergovaline, i.e. an ergoto alkaloid, was specifically detected in the endophyte-infected grasses. It thus became clear that the ergovaline causes fescue toxicosis.

As described above, when a plant, especially pasture, is infected by the endophyte, resistance to pests and disease, a growth rate and resistance to environmental factors such as heat and dryness are improved. However, the biosynthesized substances of the endophyte are poisonous to livestock, and give rise to the problems of the rye grass slugger, fescue toxicosis, etc.

In view of the problems described above, an object of the invention is to provide a plant into which the symbiotic fungus is artificially introduced, and a method of artificially introducing the symbiotic fungus into a plant. According to the present invention, the plant does not show toxicity against livestock and has strong resistance to pest.

Further objects and advantages of the invention will be apparent from the following description of the invention.

SUMMARY OF THE INVENTION

According to the present invention, a plant is artificially introduced by a symbiotic fungus whose final metabolic product is a chanoclavine. The symbiotic fungus may be a filamentous fungus belonging to the genus *Neotyphodium*. The symbiotic fungus may also be at least one of fungi deposited at Japanese National Institute of Bioscience and Human Technology under the numbers FERM P-17672 (BP-08480), FERM P-17673 (BP-08481) and FERM P-17674 (BP-08482). The plant into which the symbiotic fungus is artificially introduced may be a grass such as *Agrostis, Festuca, Poa* and *Lolium*. The plant may includes a seed of a later generation taken from these plants, a plant grown from a seed of a later generation, and a hybrid plant having these plants and seeds as parents.

According to the present invention, a method of introducing a symbiotic fungus to a plant includes the steps of isolating symbiotic fungi from a plant existing naturally; artificially cultivating the isolated symbiotic fungi; introducing the cultivated symbiotic fungi into a target plant; infecting the plant with the introduced symbiotic fungi; and selecting a plant infected with a symbiotic fungus whose final metabolic product is a chanoclavine.

According to the present invention, a method of introducing a symbiotic fungus to a plant includes the steps of isolating symbiotic fungi from a plant existing naturally; artificially cultivating the isolated symbiotic fungi; selecting a symbiotic fungus whose final metabolic product is a chanoclavine from the cultivated symbiotic fungi; introducing the selected symbiotic fungus into a target plant; and infecting the plant with the introduced symbiotic fungus.

An alkaloid metabolism of the symbiotic fungus is shown in FIG. 1. The chanoclavine is an intermediate product in the metabolism. The chanoclavine is a clavine alkaloid having the chemical structure shown in FIG. 2, and it has various pharmacological effects. Ergotoalkaloids such as ergovaline are produced from the chanoclavine. It was found that some of the symbiotic fungi searched by the inventors do not biosynthesize the ergotoalkaloids, and produce the chanoclavine as the final metabolic product. The symbiotic fungus whose final metabolic product is the chanoclavine does not show ergovaline toxicity. Accordingly, the plant infected by such a symbiotic fungus does not show the ergovaline toxicity.

In the present invention, the symbiotic fungus whose final metabolic product is the chanoclavine is used. Before and after the introduction of the fungus into the plant, the screening is performed, and the plant infected with the fungus is selected. The symbiotic fungus includes filamentous fungi of the genus *Neotyphodium* for infecting the grasses.

In the invention, such filamentous fungi are used, and the plant is infected with the filamentous fungi whose final metabolic product is the chanoclavine. Therefore, the plants do not show the ergovaline toxicity, and have improved characteristics. Also, the plants infected with the filamentous fungi whose final metabolic product is the chanoclavine accumulate a large amount of the chanoclavine in their tissues. Therefore, it is possible to provide a fungus without ergovaline or Lolitrum B by screening the fungi with the chanoclavine as a marker.

DETAILED DESCRIPTION OF PREFERRED EMBODIMENTS

Hereunder, embodiments of the present invention will be described with reference to the accompanying drawings. In the first embodiment of the invention, a plant infected with an endophyte which specifically biosynthesizes a chanoclavine is provided. The endophyte without ergotoalkaloids and Lolitrum B is screened using the chanoclavine as a marker. The embodiment will be described according to a process shown below.

Stage 1; Detection and Isolation of Endophyte (1) Detection of Endophyte

Epidermis of leaves and sheaths of plants collected in a search were peeled and stained by immersing in aniline blue staining solution. Any endophytes in the tissue were detected under an optical microscope.

(2) Isolation and Bioculture of Endophyte

Explants in which the endophytes were confirmed were sterilized, transplanted to an endophyte isolation bioculture and cultured for several months.

(3) Classification of Endophytes

The isolated endophytes were classified according to a host. Alternatively, bioculture was performed under different environmental conditions using the flat plate culture method, and a classification was made according to morphological characteristics. Alternatively, a liquid culture was performed and a classification was made according to morphological characteristics. Alternatively, a slide culture was performed and a classification was made according to morphological characteristics.

Stage 2; Introduction of Endophyte

The isolated endophytes were artificially introduced into a plant such as genuses *Agrostosis, Festuca, Lolium* and *Poa* as a target grass. The endophytes were introduced by direct inoculation of the plant, or by preparing undifferentiated cells such as callus from the plant and inoculating, and regenerating the plant from the callus. These methods may be chosen arbitrarily according to the type of plant in which the endophytes were introduced.

Stage 3; Confirmation of Endophyte Introduction

Explants taken from the individuals into which the endophytes were introduced were stained by a staining solution. An optical microscope was used for observation, and the endophyte, or presence or absence of the infection, was detected using the enzyme immunoassay technique.

Stage 4; Examination of the Plant into which the Endophytes were Introduced (1) Detection of Chanoclavine Alkaloids biosynthesized in the plant infected with the endophytes were analysed, and detection of chanoclavin, ergotoalkaloids and Lolitrum B was performed.

(2) Identification of Chanoclavine

An identification of the chanoclavine as a final metabolic product was made by determining whether the alkaloid specifically biosynthesized and collected in a large amount in the plant infected with the endophyte was chanoclavine.

(3) Pest Resistance Test

Pests considered to be harmful were bred, and a pest damage experiment was conducted artificially using the plant infected with the endophytes.

(4) Tests Using a Later Generation

Seeds in which the endophyte was present were collected and germinated. After the endophyte was confirmed, the tests described above were performed.

Stage 5; Biosynthesis of Chanoclavine on an Artificial Endophyte Bioculture Medium (1) Bioculture of Endophyte The isolated endophyte was biocultured under different environmental conditions using the flat plate culture method, and alkaloids were biosynthesized.

(2) Detection of Chanoclavine from Bioculture

Alkaloids biosynthesized from the bioculture in which the fungi alone was cultured were analysed, and chanoclavine, ergotoalkaloids and Lolitrum B were detected.

Stage 6; Screening of Endophytes Using Chanoclavine as a Marker

An endophyte was screened based on an ability to biosynthesize the chanoclavine without ergotoalkaloids or Lolitrum B in a pure fungus, or a plant infected with the fungus.

Another embodiment of the invention will be described next. In the embodiment of Stage 1-Stage 6 described above, the identification was performed as to whether or not the infecting symbiotic fungus was a fungus which biosynthesizes chanoclavine as a final metabolic product by analyzing the alkaloids biosynthesized in plants infected with the endophyte. Instead of the step, the identification was performed before artificially introducing the symbiotic fungus into the plant.

Specifically, in the embodiment, after culturing the endophyte isolated from the plants collected in a search, the alkaloids in the endophyte were analyzed, and identification was performed as to whether or not the symbiotic fungi were producing the chanoclavine as the final metabolic product. In other words, the difference from the first embodiment is that the identification of the chanoclavine is performed before introduction into the plant. The remaining features of the procedure are identical to those of the first embodiment.

Example 1

(1) Analysis of Fungi

To isolate the endophyte from the plant, the leaf and leaf sheath were washed with water, immersed in a 70% aqueous solution of ethanol for 10 seconds, immersed in a 2.5% aqueous solution of sodium hypochlorite for 10 minutes, washed three times with sterile water, transferred to an endophyte isolation culture, and cultured in the dark at 25° C.

The isolation culture was prepared by sterilizing PDA (potato dextrose agar) adjusted to pH 5.6 at 121° C. for 15 minutes, adding 100 mg/l each of penicillin and streptomycin, and pipetting 20 ml portions into plastic Petri dishes having a diameter of 9 cm.

After approx. 3-8 weeks, the mycelium was isolated from an explant, and the colonies were removed by a cork borer having a diameter of 5 mm, transferred to a PDA culture and corn meal agar culture, and grown.

(2) Classification and Identification of Endophytes by Using the Flat Plate Culture Method The mycelium transplanted to the PDA culture was grown in the dark at 25° C., and the colonies formed were examined. On examination, surfaces of the colonies on the culture were all white filaments, and their underside was also white. Their growth was relatively slow, and they grew to a radius of only about 3 cm in one month. On the corn meal agar culture, growth was much slower than on the PDA culture, the colonies growing to a radius of only about 1 cm in one month. The characteristics of the colonies were essentially identical to those of the PDA culture.

The isolated endophytes were deposited on Dec. 7, 1999 and accepted at Japanese National Institute of Bioscience and Human Technology, which belongs to the Agency of Industrial Science and Technology. The description and deposition numbers of these endophytes are as follows.

FERM P-17672 (*Neotyphodium* sp. Po-060B)
FERM P-17673 (*Neotyphodium* sp. Po-062)
FERM P-17674 (*Neotyphodium* sp. Po-120)

(3) State of Mycelium by Slide Culture

A PDA culture of thickness 2-3 mm was mounted on a glass slide, mycelium was grown on the culture, and the morphology of the mycelium and formation of conidiospores was examined. This culture was performed at 25° C. in the dark.

On the examination, it was found that all the mycelia were colorless, partitions of width 1-2 um observed throughout. All the isolated endophytes were able to form conidiospores. The conidiospores were formed at the ends of single phialides emerging from the ends or sides of the mycelium, and most were single conidiospores.

All conidiospores were colorless, and monocellular. Most conidiospores were kidney-shaped and were 3-8×1-3 um in size. The phialides formed were all cylindrical tapering towards the ends, and isolated from the mycelium by partitions.

(4) Method of Introducing the Endophyte

For the inoculation, seeds were sterilized and sown on a WA culture (Water Agar culture) comprising 0.8% agar added to water, and cultured under dark conditions. 3-7 days after starting the culture, a notch was inserted in the growth point of the plant with a knife, and mycelia cultured on the PDA medium were inserted.

After 8 days in the dark at 25° C. and 30° C., the plants were placed under illumination at 15° C. for 16 hours for 4 days, and placed under illumination at 25° C. for 16 hours for at least 2 days. Plants turned green were acclimatized in pots.

The epidermis of leaves and leaf sheaths of these plants were removed, and the presence or absence of endophyte in the tissue was confirmed by an optical microscope examination. This confirmation was performed as follows. 5 ml of lactic acid, 10 ml of glycerine, 5 ml of water and several drops of a staining solution comprising 0.02 g of an aqueous solution of aniline blue were placed on a glass slide. The leaf sheath was peeled away, and the underside epidermis was peeled away toward the leaf vein. The peeled epidermis was placed on the glass slide, covered with a cover glass, boiled in the flame of a gas burner, and the tissue was observed with an optical microscope. Under these conditions, when the endophyte is present, the mycelium appears blue, so the endophyte can be detected by this procedure.

As a result, the endophyte was detected in genuses *Agrostis, Festuca, Poa* and *Lolium*, which are grasses. From the life cycle of the fungus, the endophyte was found to be a *Neotyphodium* endophyte that is reproduced only asexually and does not leave the plant.

It was also clear that FERM P-17672, FERM P-17673 and FERM P-17674, deposited at Japanese National Institute of Bioscience and Human Technology, infected the plants belonging to genuses *Agrostis, Festuca, Poa* and *Lolium*, which are grasses.

(5) Artificial Inoculation Using Callus

Callus was induced in *Agrostis, Festuca, Poa* and *Lolium*, which are grasses, as specimens for artificial inoculation. A callus induction culture of these plants was prepared by adding 2.0 mg/l of 2,4-D(2,4-dichlorophenoxyacetic acid) and 0.2 mg/l of BAP (6-benzylaminopurine) to an MS base culture.

Seedlings obtained immediately after germination on an MS culture were transplanted to the callus induction cultures, and cultured for 2 months in the dark at 25° C. so as to obtain callus having a differentiating ability. All calluses were induced on the induction culture, and then transferred to the MS base culture without addition of plant hormone.

These plant calluses were artificially inoculated with fungus of FERM P-17672, FERM P-17673 and FERM P-17674 deposited at Japanese National Institute of Bioscience and Human Technology. Artificial inoculation was performed by taking a small amount of mycelium on an end of a knife, and transplanting it to the center of the callus.

The callus was cultured for several weeks in the dark at 25° C. and 30° C., and placed under illumination for 16 hours, or alternatively it was placed under illumination for 16 hours from the start. The regenerated plant was then transferred to a fresh MS culture and grown for one month. When an examination was made for presence of the endophyte according to the method described in (1), it was confirmed that the endophyte was introduced.

(6) Method of Screening a Fungus which Specifically Synthesizes Chanoclavine in the Plant The leaves and leaf sheaths of the plants artificially infected with FERM P-17672, FERM P-17673 and FERM P-17674 deposited at Japanese National Institute of Bioscience and Human Technology and plants infected with other freeze-dried fungi were agitated and extracted for one day and night at a room temperature by a chloroform/methanol/25% ammonia water=75/25/0.5 solution, filtered on filter paper, and evaporated. The presence of chanoclavine was confirmed with the TLC (Thin Layer Chromatography) analysis.

Figure 4A:
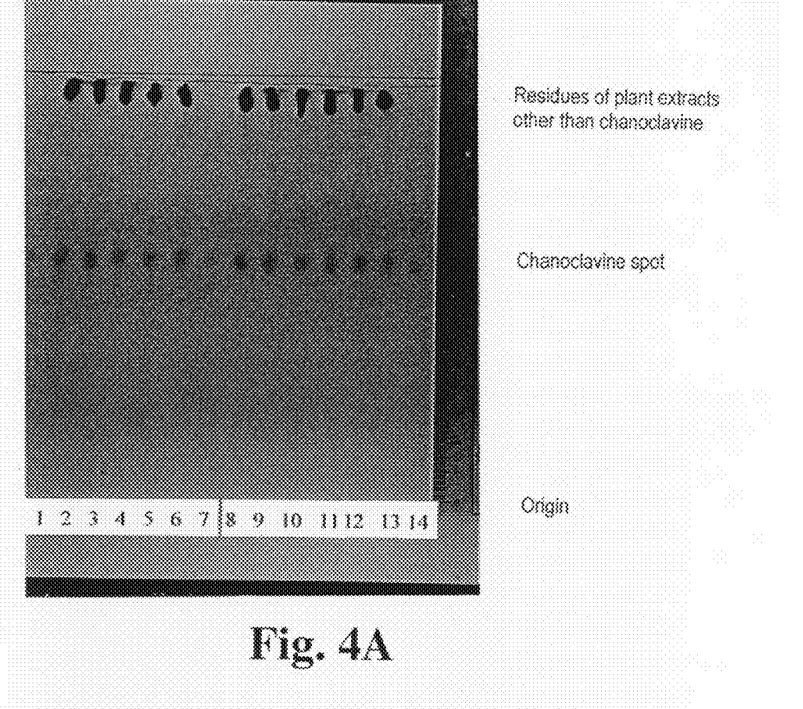
FIG. 4 is a photograph of thin layer chromatography and an analysis chart of thin layer chromatography data.
Figure 4B:
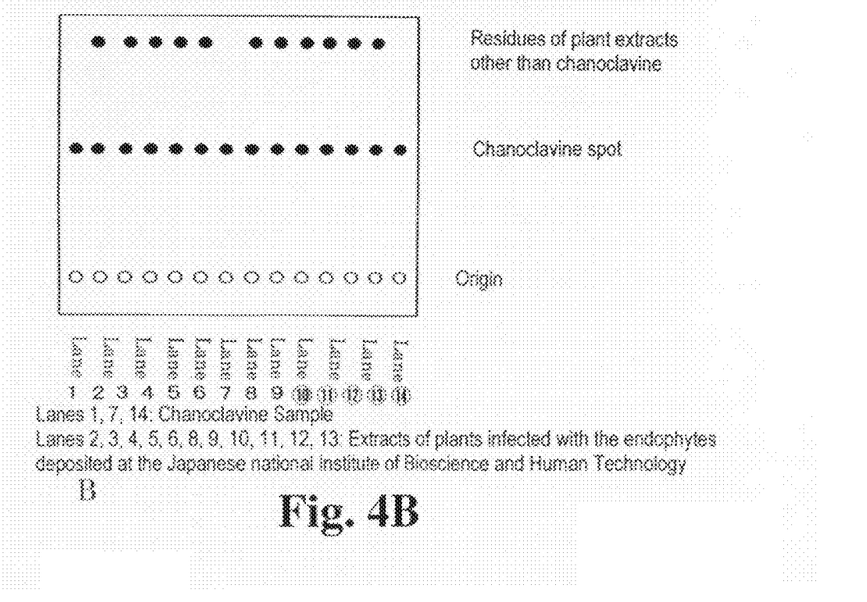

After developing on a silica gel 60 plate using chloroform/methanol/acidic acid/water=20/10/1/1 as a developing solution, a spot detected by UV and the Eherlich reagent (bluish purple coloration) having an Rf value in the vicinity of 0.5-0.6 was found by the TLC analysis as shown in FIG. 4. This spot had an identical Rf value to that of chanoclavine, and a spot having an identical Rf value was also found by the TLC analysis wherein an endophyte-infected plant extract was superimposed on the chanoclavine, as shown in FIG. 5.

Figure 5A:
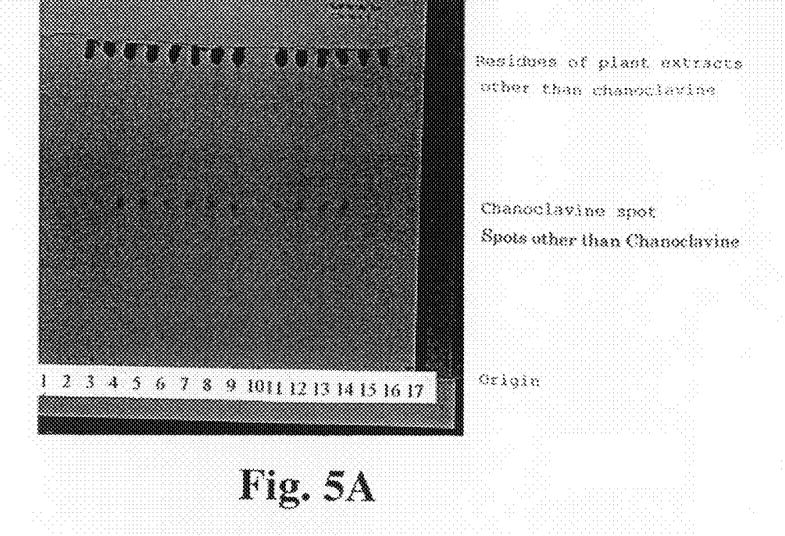
FIG. 5 is a photograph of thin layer chromatography and an analysis chart of thin layer chromatography data.
Figure 5B:
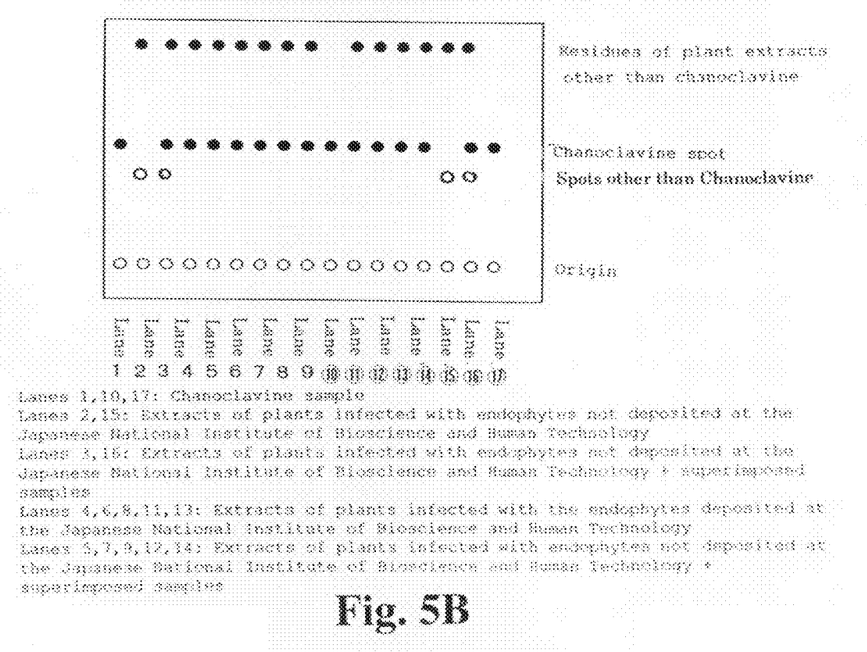

As seen in lane 2 and lane 15 in FIG. 5, a spot due to the chanoclavine was not found in the plants infected with the endophytes other than the above fungi deposited at Japanese National Institute of Bioscience and Human Technology. When the chanoclavine was superimposed on the extracts of lane 2 and lane 15 as shown by lane 3 and lane 16 in the figures, a spot due to the chanoclavine was then found as in the case of the lanes where the chanoclavine was detected.

From the above results, it is clear that the chanoclavine is biosynthesized and accumulates in the plants infected specifically with the symbiotic fungi deposited at Japanese National Institute of Bioscience and Human Technology, including *Neotyphodium* sp. FERM P-17672. Also, it was confirmed that the fungi infecting the plants could be screened for using the biosynthesis and accumulation of the chanoclavine as a marker.

For plants cultivated from the later generation seeds of the plants infected with the fungi deposited at Japanese National Institute of Bioscience and Human Technology, including *Neotyphodium* sp. FERM P-17672, the presence or absence of chanoclavine was also confirmed by the TLC analysis. It was found that even in the plants of the later generations, biosynthesis of the chanoclavine proceeded as in the case of the original plants.

(7) Method of Screening for Fungi which Specifically Synthesize Chanoclavine on Artificial Culture The endophytes, e.g. *Neotyphodium* sp. FERM P-17672, were isolated from the plants synthesizing the chanoclavine in the endophyte-infected plants. To isolate the endophyte, the leaf and leaf sheath were washed with water, immersed in a 70% aqueous solution of ethanol for 10 seconds, immersed in a 2.5% aqueous solution of sodium hypochlorite for 10 minutes, washed three times with sterile water, cut to a size of 5×5 mm, transferred to an endophyte isolation culture, and cultured in the dark at 25° C.

The isolation culture was prepared by adding 100 mg/l each of penicillin and streptomycin to PDA (potato dextrose agar), and pipetting 20 ml portions into plastic Petri dishes having a diameter of 9 cm.

At 3-8 weeks after starting the bioculture, the mycelium was isolated from plant tissue, and biocultured on a liquid culture medium. The biomedium was a PD (potato dextrose) medium, a M102 medium or an SM medium known to be an ergotoalkaloid-producing medium. 5×5 mm clumps of mycelia isolated on the PDA medium were introduced into 100 ml of the above biomedia, and cultured for from 2 weeks to as long as 6 months.

To confirm the biosynthesis of the chanoclavine, the biocultures were freeze-dried as in the case of the plants, introduced into a chloroform/methanol/25% ammonia water=75/25/0.5 solution, agitated and stirred for one day and night at a room temperature, filtered on a filter paper, and evaporated. TLC was then performed.

After developing on a silica gel 60 plate using chloroform/methanol/acidic acid/water=20/10/1/1 as a developing solution, a spot detected by UV and the Eherlich reagent (bluish purple coloration) having an Rf value in the vicinity of 0.5-0.6 was found by the TLC analysis as in the above case, showing that the chanoclavine was biosynthesized.

(8) Identification of Chanoclavine

The freeze-dried endophyte-infected plants, for example, the plants infected with FERM P-17672, FERM P-17673 and FERM P-17674 deposited at Japanese National Institute of Bioscience and Human Technology, and the leaves and leaf sheaths of uninfected individuals were extracted by shaking for at least 30 minutes at a room temperature with an 80% aqueous solution of methanol. The extract was filtered on a filter paper, the filtrate supplied to a VARIAN BOND ELUT CBA column packed with a negative ion exchange resin (AG2×8 200-400 mesh) suspended in an 80% aqueous solution of methanol substituted by 25% ammonia water, and rinsed with pure water. The filtrate was solved by a 5% formic acid solution, and the obtained fractions were provided for the TLC analyses (Thin Layer Chromatography) and HPLC (High Performance Liquid Chromatography).

Figure 6:
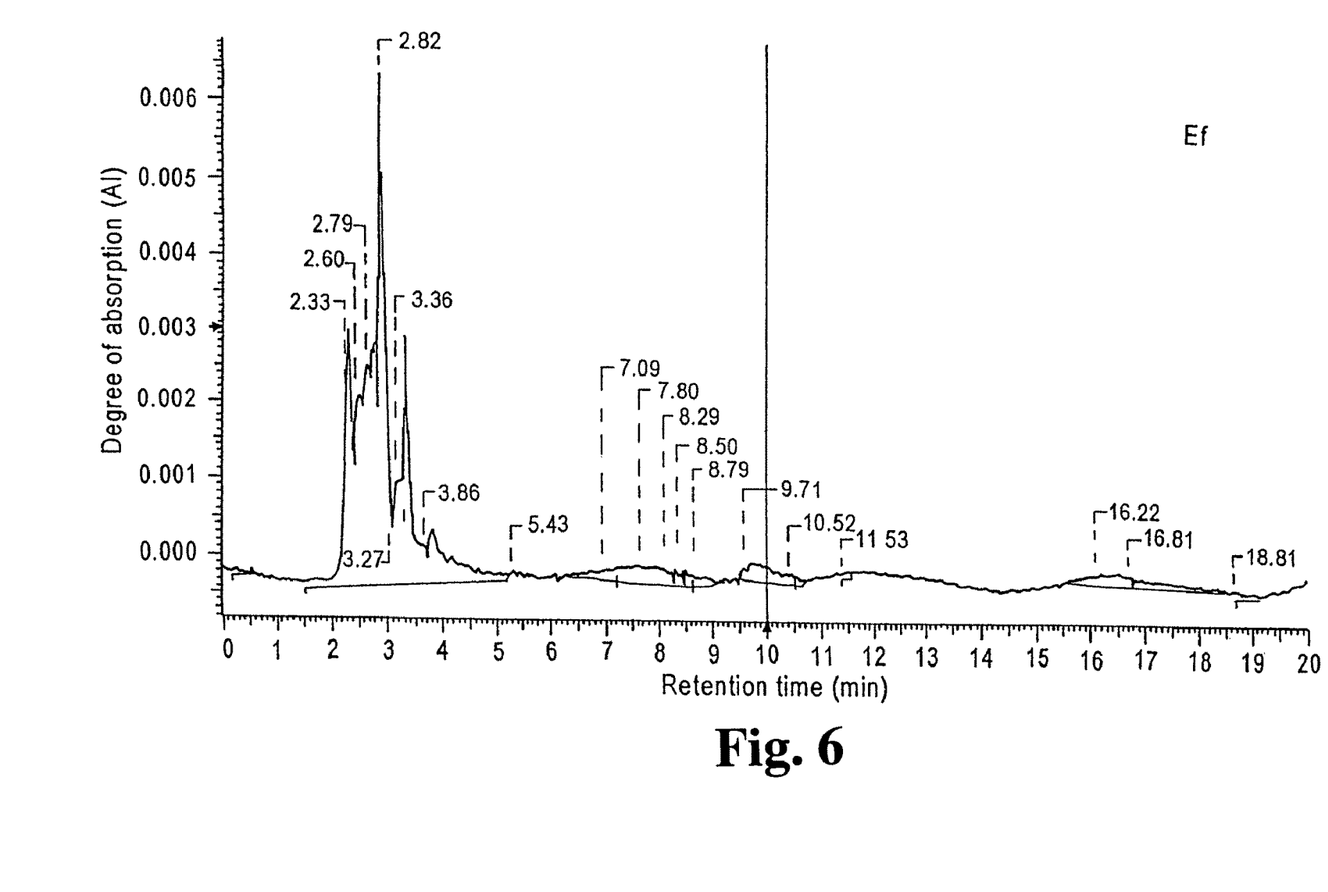
FIG. 6 is a graph showing a result of high performance liquid chromatography.
Figure 7:
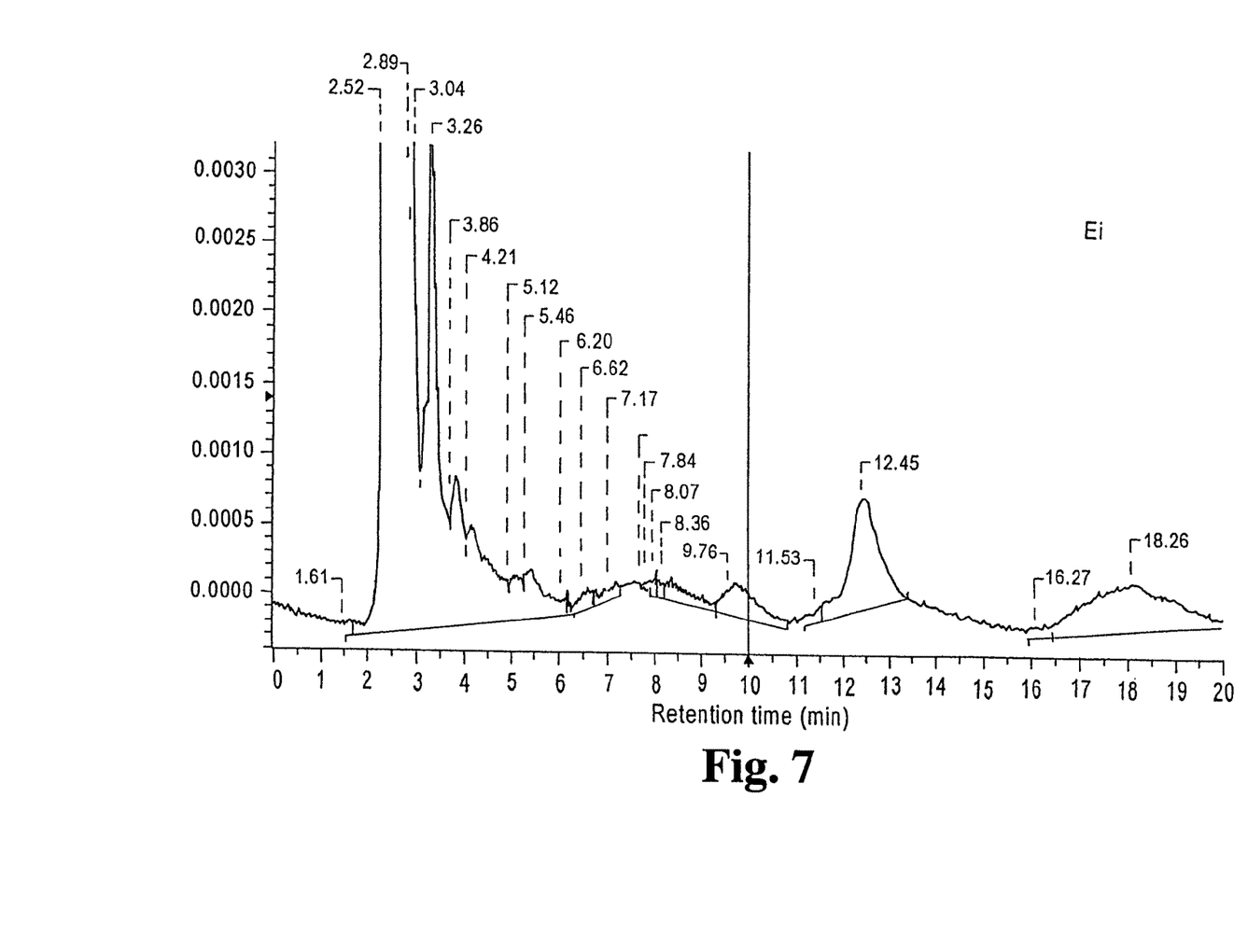
FIG. 7 is a graph showing a result of high performance liquid chromatography.

When the obtained fractions were analyzed by HPLC using a C18 column (5 um particle size, 100×8 mm) and UV at 280 nm, a specific significant peak was obtained in the vicinity of a retention time in the vicinity of 12 minutes as shown in FIG. 7 only for the fractions obtained from the endophyte-infected plants. In the case of the plants not infected by the endophytes, this peak was not found, as shown in FIG. 6.

After developing using a silica gel 60 plate and a developing solution of chloroform/methanol/acetic acid/water=20/10/1/1, a spot detected by UV and the Eherlich reagent (bluish purple coloration) having an Rf value in the vicinity of 0.5-0.6 was found by the TLC analysis. The spot found was also specific for the endophyte-infected plants, and was not observed for the uninfected individuals.

This fraction was isolated by HPTLC. As a result, the recovery rate was 0.06-0.08% on average from the freeze-dried samples. This fraction was also tested positive in fluorescent light detection by HPLC, suggesting an indole structure. Hence, the NMR, MS and IR (infrared analysis) were measured.

Figure 2:
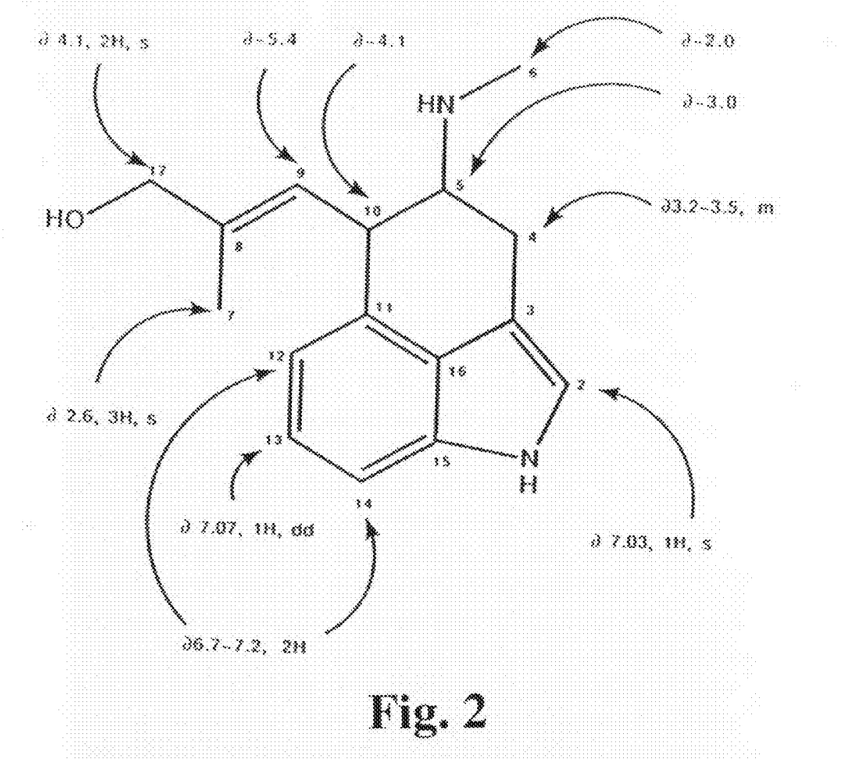
FIG. 2 is a structural view showing a chemical structure of chanoclavine.
Figure 3:
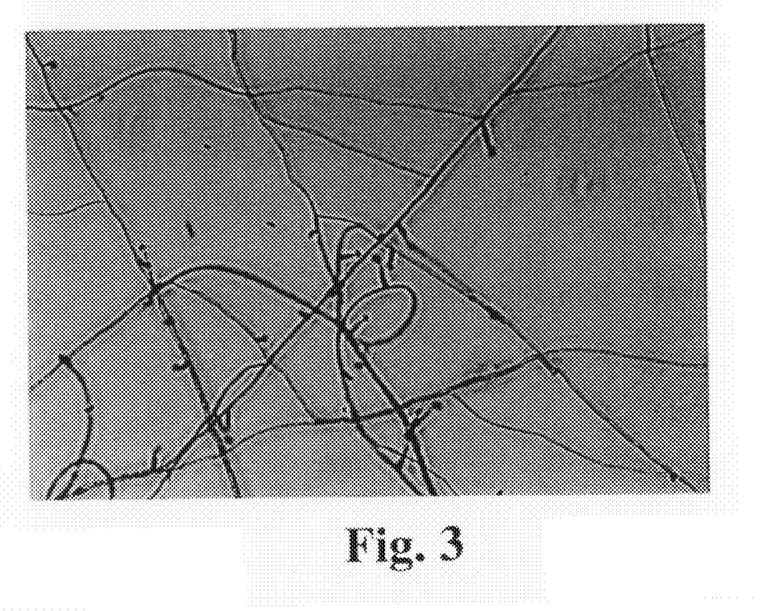
FIG. 3 is a photograph showing morphology of a filamentous fungus.

As a result of FD-MS (Field Dissociated Ionization Molecular Weight Measurement), M+256 was observed. Further, in addition to the fragment ions of a molecular peak at 256 in EI-MS, a fragmentation pattern specific to clavine alkaloids such as m/z 237 due to —H3O+ and m/z 155, 154 due to tricyclic stable ions was observed. When the examination was performed from the molecular formula suggested by EI-HR-MS, it was found that the chanoclavine corresponded to the molecular formula and the fragmentation pattern in EI. When NMR measurements were assigned as shown in FIG. 2, the isolated fragments were identified as chanoclavine. In the IR, absorptions were seen at 3400 (—OH), 1605 (C═C), 1420 and 1380 cm$^{-1}$.

(9) Identification of Ergovaline

It was examined whether or not the endophytes, i.e. symbiotic fungi living in the endophyte-infected plants, produce ergovaline. The leaves and sheaths of freeze-dried plants infected with the endophytes were extracted by shaking for at least 30 minutes at a room temperature with a mixed solution of 0.01 N aqueous sodium hydroxide solution:chloroform=1:9. The extract was filtered on a filter paper. The filtrate was supplied to a silica gel column (Water Sep-Pak Plas Silica) conditioned with chloroform, and rinsed with chloroform. Fractions were eluted by a mixture of acetone:chloroform: acetic acid=80:20:0.05. The eluate was concentrated, dried and solidified, re-eluted with a 33% aqueous solution of methanol containing 0.1% ascorbic acid, and submitted for HPLC (High Performance Liquid Chromatography).

Figure 8:
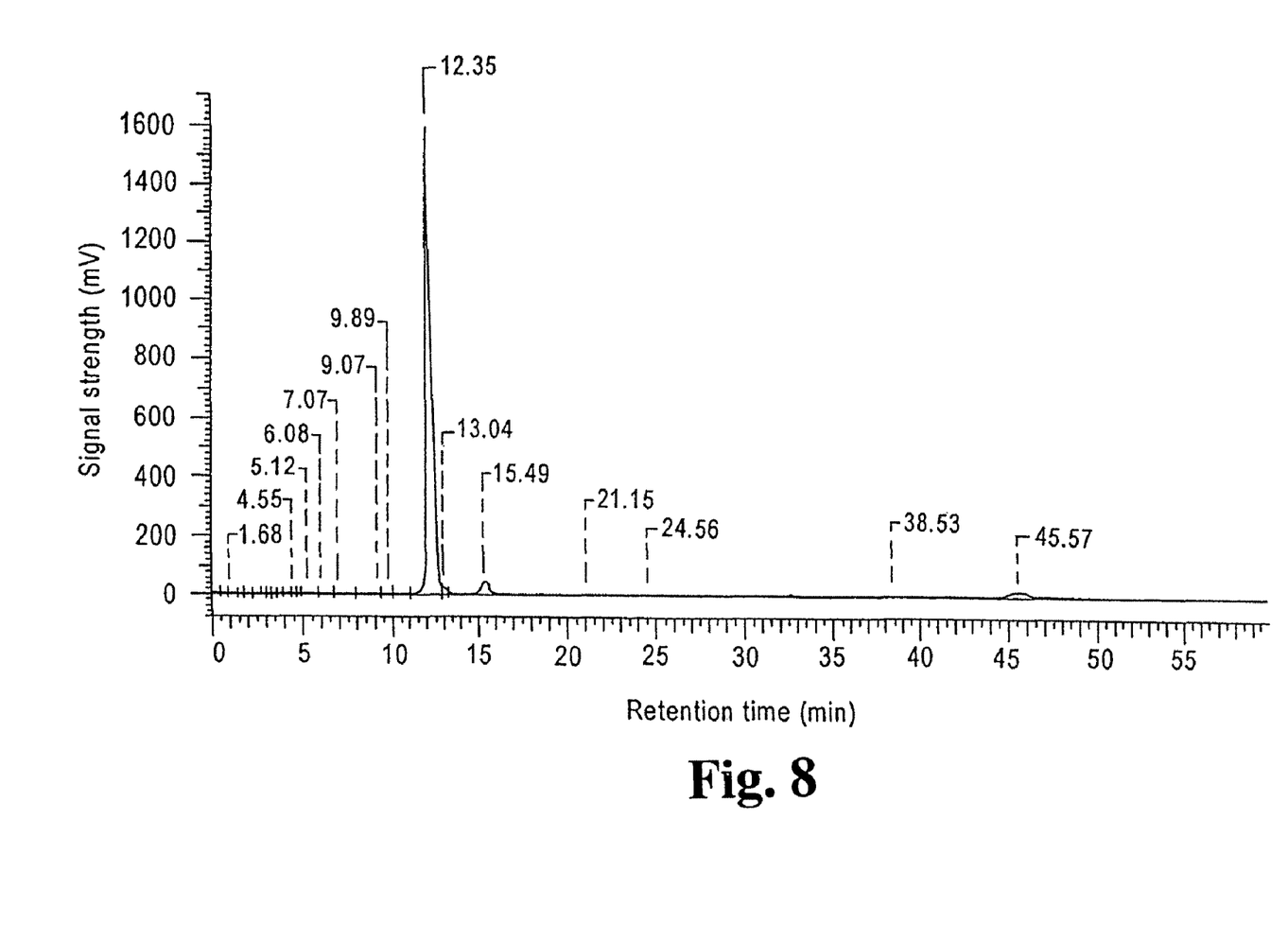
FIG. 8 is a graph showing a result of high performance liquid chromatography.

In the HPLC analysis, fluorescence detection was performed using a C18 column (3 um particle size, 4.6×7.5 mm), Ex (excitation wavelength) 310 nm and Em (fluorescence wavelength) 415 nm. When ergovaline tartrate, i.e. a sample of ergovaline, was analysed by HPLC, an ergovaline peak was observed in the vicinity of a retention time of 12 minutes as shown in FIG. 8. In other words, sample ergovalines showed a retention time peak at 12.35.

Figure 9:
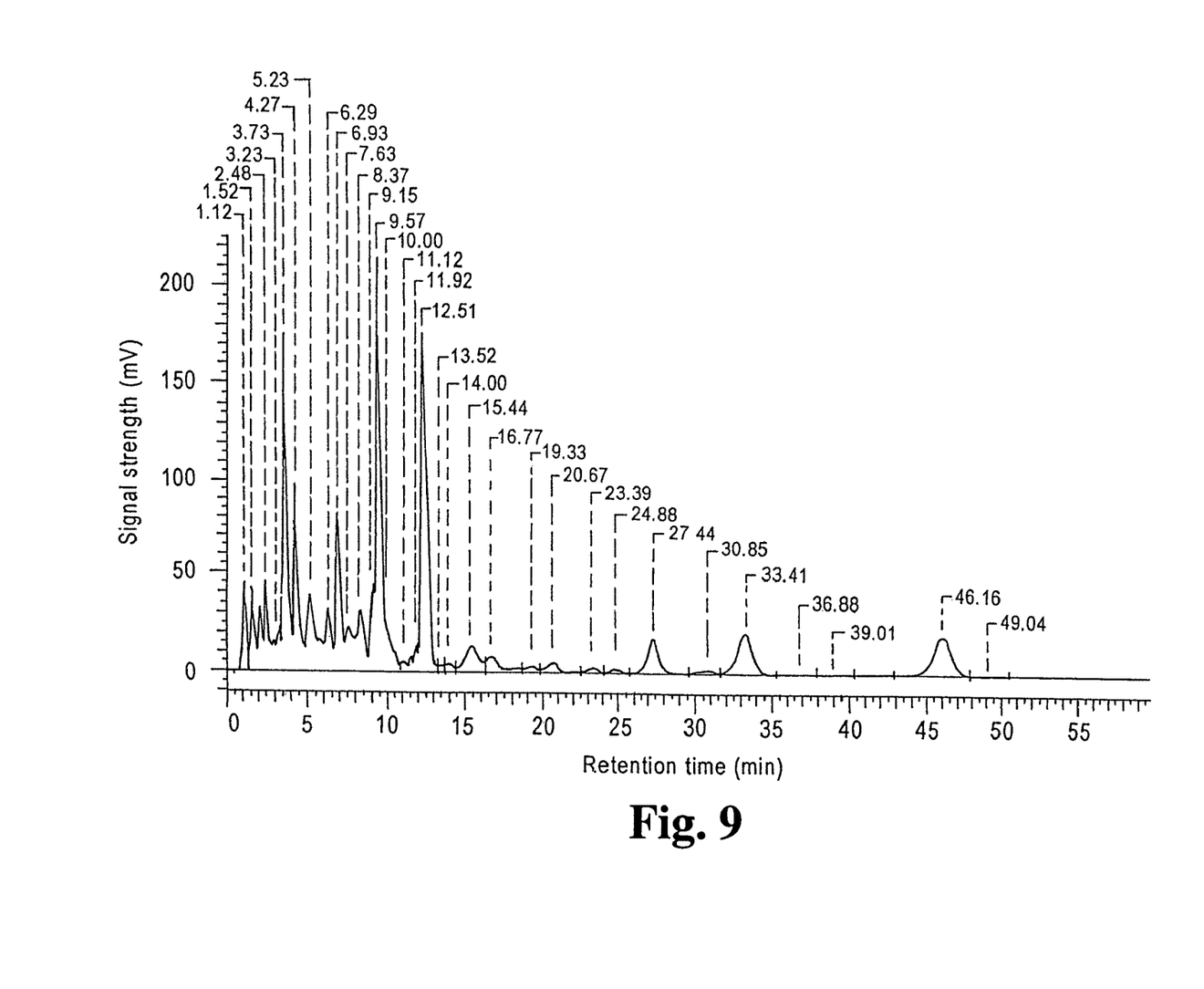
FIG. 9 is a graph showing a result of high performance liquid chromatography.

The presence of ergovaline biosynthesis in the endophyte-infected plants was determined by observing whether or not, in the case of the eluate obtained by the above method from the endophyte-infected plants, there was a peak in the vicinity of a retention time of 12 minutes as for the samples in the HPLC analysis. As a result, for the endophyte-infected plants other than those deposited at Japanese National Institute of Bioscience and Human Technology, the ergovaline was detected in the order of approximately 1 ppm (per dry weight) in the vicinity of a retention time of 12 minutes, as shown in FIG. 9. Specifically, for the endophyte-infected plants other than those deposited at Japanese National Institute of Bioscience and Human Technology, a peak was found near the same retention time as for the sample ergovaline, i.e. at 12.51 minutes, thereby confirming the ergovaline. The concentration was approximately 1 ppm per dry weight.

Figure 10:
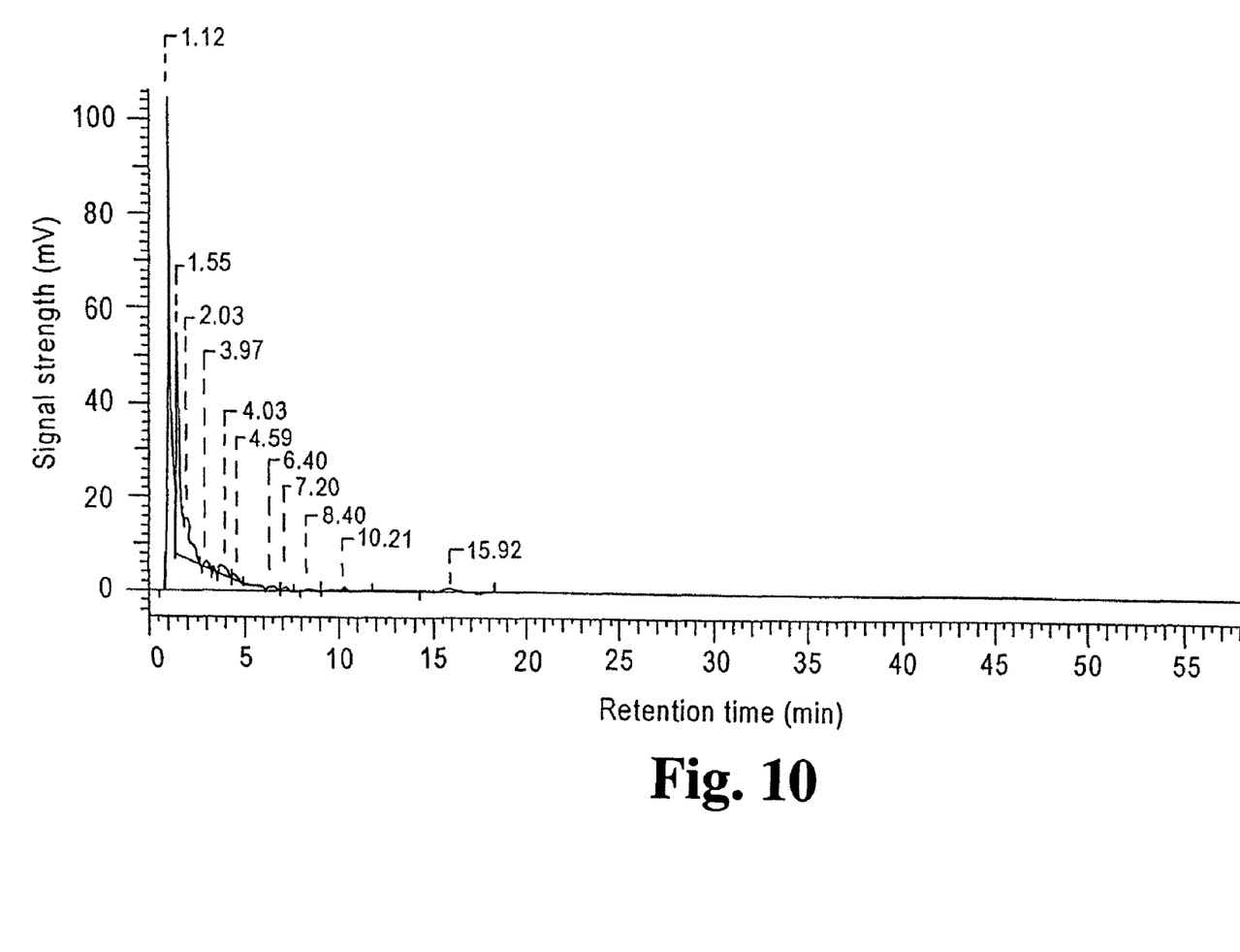
FIG. 10 is a graph showing a result of high performance liquid chromatography.

On the other hand, when HPLC analysis was performed in an identical method using the plants infected with FERM P-17672 deposited at Japanese National Institute of Bioscience and Human Technology, the ergovaline was not detected, as shown in FIG. 10. Specifically, for the plants infected with FERM P-17672 deposited at Japanese National Institute of Bioscience and Human Technology, there was no peak at all in the vicinity of a retention time of 12 min, thereby confirming that the ergovaline was not produced. From the above results, it was clear that the plants infected with FERM P-17672 do not biosynthesize the ergovaline, i.e. a toxic substance to livestock. Identical results were obtained for FERM P-17673, FERM P-17674.

(10) Comparative Test of Pest Resistance with Other Fungi

A test of resistance to webworm, a major pest in pasture grass, was performed using plants belonging to the genus *Poa* infected with, for example, *Neotyphodium* sp. FERM P-17672 with the above method, and plants infected with fungus strains other than the fungi deposited at Japanese National Institute of Bioscience and Human Technology.

Figure 11:
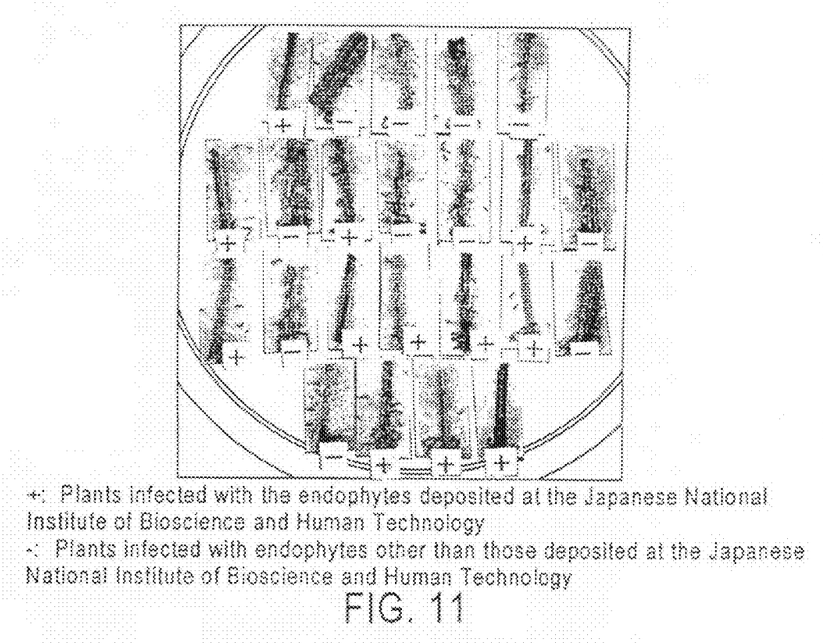
FIG. 11 is a photograph showing a result of a pest resistance test.
Figure 12:
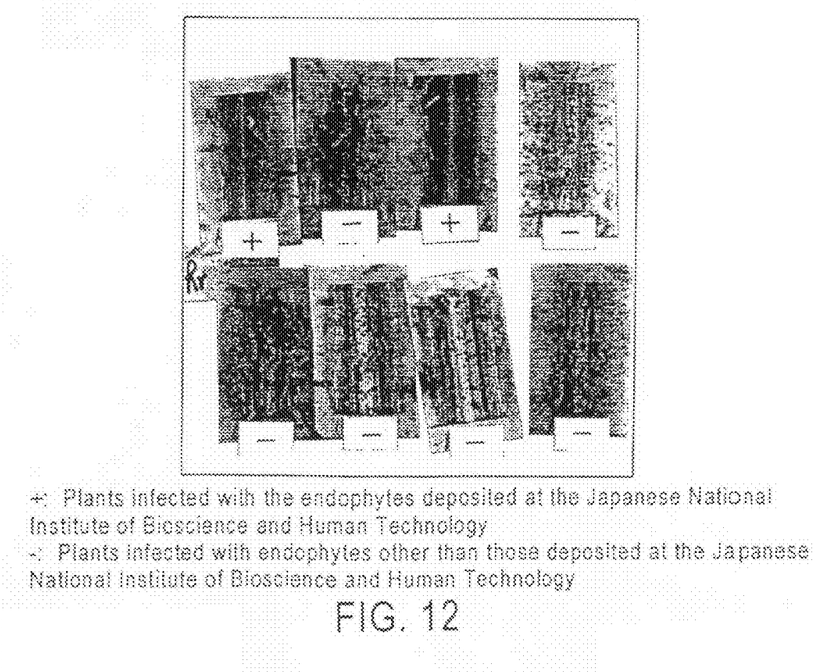
FIG. 12 is a photograph showing a result of the pest resistance test.

The pest resistance test was performed by releasing approximately 200 webworm larvae immediately after hatching in Petri dishes with a diameter of 9 cm containing respectively the above leaf sections, leaving the dishes in a room at 25° C., and examining an extent of damage after 24 hours and again after 48 hours. After 48 hours, whereas almost all the plants infected with fungi other than the fungi deposited at Japanese National Institute of Bioscience and Human Technology were consumed, the plants infected with *Neotyphodium* sp. FERM P-176723 had practically all their leaves remaining and showed strong resistance. The results obtained for *Poa* and *Lolium* are respectively shown in FIG. 11 and FIG. 12.

The resistance test against the webworm was performed for plants of the genus *Lolium* infected with FERM P-17672 and fungus strains other than those deposited at Japanese National Institute of Bioscience and Human Technology in the same way as for the plants of the genus *Poa*.

When the extent of the damage due to the webworm was examined 24 hours after starting the test, it was found that, as in the case of the plants belonging to the genus *Poa*, whereas the plants infected with fungus strains other than those deposited at Japanese National Institute of Bioscience and Human Technology were practically consumed, the plants infected with FERM P-17672 still had practically all their leaves, and showed strong resistance.

The results were identical when the other fungi deposited at Japanese National Institute of Bioscience and Human Technology, FERM P-17673 and FERM P-17674, were used. From the above results, it was confirmed that FERM P-17672, FERM P-17673 and FERM P-17674 deposited at Japanese National Institute of Bioscience and Human Technology imparted strong pest resistance to the plants with which they are infected, as shown in Table 1.

Example 2

In this example, the endophytes were screened by the screening method (7) in Embodiment 1 before infecting the plant, and the endophytes were selected when the endophytes biosynthesized and produced the chanoclavine as the final metabolic product. The symbiotic fungi screened in this way were then used to infect the same plants as those in Embodiment 1, i.e. the grasses *Agrostis, Festuca, Poa* and *Lolium*, with the method of (4) in Embodiment 1. When the screening was performed according to the method of (6) in Embodiment 1, it was confirmed that the plants were infected with the symbiotic fungi producing the chanoclavine as the final metabolic product. When the pest resistance test was performed on these plants according to the method of (10) in Embodiment 1, it was found that a substantially identical effect to that in Embodiment 1 was obtained.

While the invention has been explained with reference to the specific embodiments of the invention, the explanation is illustrative and the invention is limited only by the appended claims.

Example 1

TABLE 1

Characteristics of fungus belonging to the genus *Neotyphodium* (FERM P-17672 deposited at the Japanese National Institute of Bioscience and Human Technology)

| Plant species | Infection of plant | Chanoclavine production in plant | Chanoclavine production on artificial culture | Seed propagation | Infection of plants raised from seed | Pest resistance to webworm |
|---|---|---|---|---|---|---|
| *Agrostis* | | | | | | |
| A. alba | +[1] | + | + | + | + | + |
| A. canina | + | + | + | + | + | + |
| A. palustris | + | + | + | + | + | + |
| A. tenuis | + | + | + | + | + | + |
| *Festuca* | | | | | | |
| F. arundinacea | + | + | + | + | + | + |
| F. ovina | + | + | + | + | + | + |
| F. o. var. duriuscula | + | + | + | + | + | + |
| F. pratensis | + | + | + | + | + | + |
| F. rubra | + | + | + | + | + | + |
| F. r. var commutata | | | | | | |
| *Lolium* | | | | | | |
| L. multiflorum | + | + | + | + | + | + |
| L. perenne | + | + | + | + | + | + |
| *Poa* | | | | | | |
| P. compressa | + | + | + | + | + | + |
| P. pratensis | + | + | + | + | + | + |
| P. trivialis | + | + | + | + | + | + |

[1]+ signifies "yes"

What is claimed is:

1. A method of introducing a symbiotic fungus producing chanoclavine as the final metabolic product into a plant, comprising the steps of:
    isolating symbiotic fungi from naturally existing plants,
    artificially cultivating the isolated symbiotic fungi,
    introducing the cultivated symbiotic fungi into target plants,
    infecting the target plants with the introduced symbiotic fungi,
    determining whether the introduced symbiotic fungi infecting the target plants produce the chanoclavine as the final metabolic product, and
    selecting the target plants which produce the chanoclavine as the final metabolic product,
    wherein said symbiotic fungus is one selected from the group consisting of FERM BP-08480, FERM BP-08481 and FERM BP-08482 deposited at the Japanese National Institute of Bioscience and Human Technology.

2. A method according to claim 1, wherein said plant is a grass selected from the group consisting of *Agrostis, Festuca, Poa* and *Lolium*.

3. A method according to claim 1, wherein said symbiotic fungi infected in the target plants and producing the chanoclavine as the final metabolic product are selected by screening using chanoclavine as a marker.

4. A method according to claim 3, wherein said screening is performed by thin layer chromatography using chanoclavine as a marker.

5. A method according to claim 3, wherein said screening is performed by liquid chromatography using chanoclavine as a marker.

6. A method of introducing a symbiotic fungus producing chanoclavine as the final metabolic product into a plant, comprising the steps of:
    isolating symbiotic fungi from naturally existing plants,
    artificially cultivating the isolated symbiotic fungi,
    selecting one of the isolated symbiotic fungi producing the chanoclavine as the final metabolic product,
    introducing the selected symbiotic fungus into the plant, and
    infecting the plant with the introduced symbiotic fungus,
    wherein said symbiotic fungus is one selected from the group consisting of FERM BP-08480, FERM BP-08481 and FERM BP-08482 deposited at the Japanese National Institute of Bioscience and Human Technology.

7. A method according to claim 6, wherein said plant is a grass selected from the group consisting of *Agrostis, Festuca, Poa* and *Lolium*.

8. A method according to claim 6, wherein said symbiotic fungi producing the chanoclavine as the final metabolic product is selected by screening using chanoclavine as a marker.

9. A method according to claim 8, wherein said screening is performed by thin layer chromatography using chanoclavine as a marker.

10. A method according to claim 8, wherein said screening is performed by liquid chromatography using chanoclavine as a marker.

* * * * *